(12) United States Patent
Berglund et al.

(10) Patent No.: US 8,981,166 B2
(45) Date of Patent: Mar. 17, 2015

(54) EXTRACTION OF FUSEL ALCOHOLS FROM ETHANOL FERMENTATION PRODUCTS

(75) Inventors: Kris A. Berglund, Okemos, MI (US); Peter K. Rossman, Chicago, IL (US)

(73) Assignee: Working Bugs, LLC, East Lansing, MI (US)

( * ) Notice: Subject to any disclaimer, the term of this patent is extended or adjusted under 35 U.S.C. 154(b) by 0 days.

(21) Appl. No.: 14/131,256

(22) PCT Filed: Jul. 13, 2012

(86) PCT No.: PCT/US2012/046592
§ 371 (c)(1),
(2), (4) Date: Apr. 15, 2014

(87) PCT Pub. No.: WO2013/010055
PCT Pub. Date: Jan. 17, 2013

(65) Prior Publication Data
US 2014/0221701 A1    Aug. 7, 2014

Related U.S. Application Data

(60) Provisional application No. 61/572,340, filed on Jul. 14, 2011.

(51) Int. Cl.
C07C 29/84   (2006.01)
C07C 29/86   (2006.01)
C07C 29/74   (2006.01)
B01D 11/04   (2006.01)
B01D 3/00    (2006.01)

(52) U.S. Cl.
CPC ............. C07C 29/74 (2013.01); B01D 11/0426 (2013.01); B01D 11/0488 (2013.01); B01D 3/009 (2013.01)
USPC .......................................... 568/913; 568/918

(58) Field of Classification Search
CPC ......... C07C 29/84; C07C 29/86; B01D 11/04
USPC .................................................. 568/913, 918
See application file for complete search history.

(56) References Cited

U.S. PATENT DOCUMENTS 2,950,288 A    8/1960  Calam et al.
6,506,430 B1   1/2003  Zimlich, III et al.
2010/0279367 A1  11/2010  Weber

OTHER PUBLICATIONS

Saha et al. "Iso-Amyl Acetate Synthesis by Catalytic Distillation" by Saha et al. International Journal of Chemical Reactor Engineering, vol. 3, Issue 1, pp. 1-3 ISSN (Online) Jul. 2005; Abstract.
International Search Report dated Sep. 21, 2012 for PCT/US2012/046592.

*Primary Examiner* — Sikarl Witherspoon
(74) *Attorney, Agent, or Firm* — Butzel Long

(57) ABSTRACT

An improved process for extracting fusel alcohols and/or fusel alcohol esters from an ethanol fermentation product involves adding to the fermentation product an extractant solvent selected from amyl alcohols, amyl acetates, and mixtures thereof to produce a two-phase system including a water and alcohol phase, and an immiscible second phase comprised of amyl alcohols, amyl acetates or a mixture thereof. Thereafter, the first and second phases can be separated to obtain a first phase depleted of fusel alcohols and/or esters of fusel alcohols and a second phase containing fusel alcohols and/or esters of fusel alcohols extracted from the first phase.

20 Claims, 3 Drawing Sheets

EXTRACTION OF FUSEL ALCOHOLS FROM ETHANOL FERMENTATION PRODUCTS

CROSS-REFERENCE TO RELATED APPLICATIONS

This application claims the benefit of PCT Application No. PCT/US2012/046592 filed Jul. 13, 2012 and U.S. Provisional Application No. 61/572,340 filed Jul. 14, 2011, which are hereby incorporated by reference in their entireties.

FIELD OF THE DISCLOSURE

This disclosure relates to an improved process for separating fusel alcohol and ethanol fermentation products using liquid-liquid extraction and optionally production of fusel alcohol esters.

BACKGROUND OF THE DISCLOSURE

The most common method for production of ethanol by fermentation of sugars utilizes strains of *Saccharomyces cerevisiae* yeast. The predominant product of such fermentations is ethanol and selectivity can reach over 99%, but other byproducts can be formed. The process of byproduct formation by yeast has recently been reviewed (Hazelwood et al., 2008). The main byproducts are called "fusel oils" or "fusel alcohols" and they consist of higher carbon number alcohols such as n-propanol, isobutanol, isoamyl alcohol, and optically active amyl alcohol. The predominant fusel alcohol is isoamyl alcohol.

There is a market for fusel alcohols and their esters in solvents, flavors and fragrances. These applications generally are for lower volumes than for fuel ethanol and represent an economically important alternative to simply leaving them in the final fuel alcohol.

During the distillation of ethanol containing mashes, there is an accumulation of the fusel alcohols on specific trays of the column (Guymon, 1958). Although, the overall amount of fusel alcohols may not exceed 1%, there are points in the column where they can be as high as 15%. The conventional approach to recovery of fusel alcohols is the use of decantation, which is accomplished by the addition of large volumes of water to cause a phase separation with the upper, lower density phase being enriched with the fusel alcohols (Guymon, 1958). The main problem with this approach is that the water rich phase contains a significant amount of ethanol and must be returned to the distillation column for recovery. The large volume of added water, usually twice as much water by volume is added to the initial fusel alcohol rich stream coming from the column, creates a large energy load on the process. This added water must be removed from the resulting mixture at significant cost. Furthermore, the added volume is also a problem causing a bottleneck in the process.

Reactive distillation has been shown to be effective in the recovery of fusel alcohol esters (Kucuk and Ceylan, 1998; Saha et al., 2005). In this process the fusel alcohols are converted to esters in the presence of a solid acid catalyst, such an ion exchange resin, in a distillation column. The esterification reaction is an equilibrium reaction, $$RCO_2H + R'OH \leftrightarrows RCO_2R' + H_2O$$

wherein it can be seen that water promotes the reverse reaction, inhibiting ester formation. This factor makes it preferable to have a low water content in the reaction mixture. A typical fusel alcohol containing stream from an ethanol distillation column can contain as much as 40% water, which would significantly impede esterification.

To summarize, there are two main obstacles that need to be addressed. A first objective is to efficiently recover fusel alcohols from an ethanol plant distillation column without introducing large quantities of water to the system. A second objective is to exclude as much water as possible from a reaction mixture for production of fusel alcohol esters.

SUMMARY OF THE DISCLOSURE

Disclosed is a process for liquid-liquid separation of fusel alcohols and esters of fusel alcohols in admixture with an ethanol in water solution as a first phase, which comprises: (a) adding an extractant solvent selected from the group consisting of an amyl alcohol, an amyl acetate and mixtures thereof as a second phase, thereby extracting the fusel alcohols and esters of fusel alcohols from the first phase into the second phase; (b) separating the first and second phases; and (c) separating the extractant solvent from the second phase. The extractant can be amyl acetate and/or isoamyl acetate. The extracted fusel alcohols can include amyl alcohol, such as a mixture of 2-methyl-butanol and 3-methyl-butanol. The first phase can comprise fusel oil from an ethanol fermentation process. In the process, at least 90% of the fusel oil can be extracted from the first phase. The ratio of the first phase to the second phase can be between about 1:2 to 4:1 by volume.

There is also disclosed an extraction using higher alcohols and esters, as opposed to decantation, for the recovery of isoamyl alcohol and other fusel alcohols from an ethanol production plant, wherein water is not introduced in the decantation step which causes a significant energy load on the overall process. Still further, the isoamyl acetate is used as the extractant ester to provide for high recovery of fusel alcohols and leaving ethanol in the aqueous phase which is recycled back into the ethanol production process. Further, the isoamyl alcohol is the alcohol extractant for recovery of fusel alcohols. Still further, the isoamyl acetate extractant can be produced by reactive distillation, and recycled for use in extraction, with a portion being product. Finally, the ethanol in water containing fusel oils streams are from Distilled Spirits Plants and Alcohol Fuel Plants.

DETAILED DESCRIPTION OF PROCESS AND EXAMPLES

Figure 1:
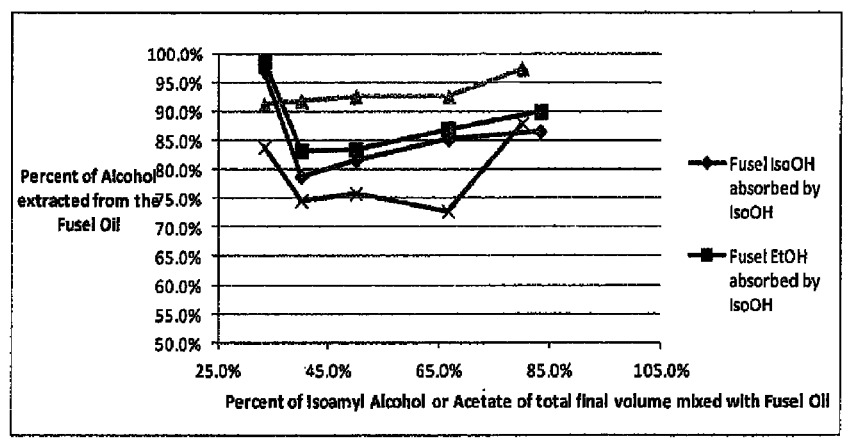
FIG. 1 is a graph showing the relative efficiency of extraction of isoamyl alcohol and ethanol from a fusel stream by isoamyl alcohol and isoamyl acetate.

In order to replace the decantation process, it was decided to attempt to develop an extraction process, wherein the isoamyl alcohol could be extracted from the fusel mixture. A key decision was to consider extractants that would be the same as products that were to be produced, namely, isoamyl alcohol and isoamyl acetate.

The term "amyl alcohol" refers to normal amyl alcohol (1-pentanol), isoamyl alcohol (3-methyl-1-butanol), active amyl alcohol (2-methyl-1-butanol), neopentyl alcohol (2,2-dimethyl-1-propanol), diethyl carbinol (3-pentanol), methylisopropyl carbinol (3-methyl-2-butanol), methyl (n) propyl carbinol (2-pentanol), and dimethylethyl carbinol (2-methyl-2-butanol).

The initial conditions for the two phases using isoamyl alcohol as the extractant are shown in Table 1. The fusel oil stream was taken from a fuel ethanol plant and is representative of a commercial stream.

TABLE 1

Initial compositions of the fusel stream to be extracted and extractant isoamyl alcohol
Initial Concentrations Before Mixing

|  |  | v/v % | mass % |
|---|---|---|---|
| Fusel Oil | | | |
| Ethanol | 383.755 g/L | 48.64% | 43.42% |
| ⅔Methyl 1-Butanol | 56.065 g/L | 6.90% | 6.34% |
| isobutanol | 0.779 g/L | 0.10% | 0.09% |
| n-butanol | 1.299 g/L | 0.16% | 0.15% |
| n-Pentanol | 0 g/L | 0.00% | 0.00% |
| Water | 441.9975 g/L | 44.20% | 50.01% |
| Total | 883.8955 | | |
| Isoamyl Alcohol | | | |
| Ethanol | 0 g/L | 0.00% | 0.00% |
| ⅔Methyl 1-Butanol | 755.59 g/L | 93.05% | 91.58% |
| isobutanol | 0 g/L | 0.00% | 0.00% |
| n-butanol | 0 g/L | 0.00% | 0.00% |
| n-Pentanol | 0 g/L | 0.00% | 0.00% |
| Water | 69.47044 g/L | 6.95% | 8.42% |
| Total | 825.0604 | | |

The results for the extraction experiments are shown in Table 2. As can be seen from the data, there is a significant reduction of the isoamyl alcohol in the aqueous phase.

A similar experiment was conducted using isoamyl acetate as the extractant. The initial conditions are shown in Table 3. It is important to note the isoamyl alcohol was produced by esterification of fusel alcohols and is representative of an unpurified ester stream that would result.

TABLE 3

Initial compositions of the fusel stream to be extracted and extractant isoamyl acetate.
Initial Concentrations

|  |  | volume % | mass % |
|---|---|---|---|
| Fusel Oil | | | |
| Ethanol | 383.755 g/L | 48.64% | 43.42% |
| ⅔Methyl 1-Butanol | 56.065 g/L | 6.90% | 6.34% |
| isobutanol | 0.779 g/L | 0.10% | 0.09% |
| n-butanol | 1.299 g/L | 0.16% | 0.15% |
| n-Pentanol | 0 g/L | 0.00% | 0.00% |
| Water | 441.9975 g/L | 44.20% | 50.01% |
| Total | 883.8955 | | |
| Isoamyl Acetate | | | |
| Ethanol | 4.835 g/L | 0.61% | 0.55% |
| ⅔Methyl 1-Butanol | 84.409 g/L | 10.40% | 9.57% |
| isobutanol | 0 g/L | 0.00% | 0.00% |
| n-butanol | 0 g/L | 0.00% | 0.00% |
| n-Pentanol | 0 g/L | 0.00% | 0.00% |
| Isoamyl Acetate | 689.376 g/L | 78.70% | 78.20% |
| n-butyl Acetate | 0.16 g/L | 0.02% | 0.02% |
| Water | 102.7785 g/L | 10.28% | 11.66% |
|  | 881.5585 | | |

TABLE 2

Summary of isoamyl alcohol extraction experiments after phase separation

| | Ratio of Fusel Oil to isoamyl Alcohol (solvent) | | | | | | | |
|---|---|---|---|---|---|---|---|---|
| | 1 to 5 | 1 to 2 | 1 to 1 | 1.5 to 1 | 2 to 1 | 3 to 1 | 4 to 1 | 5 to 1 |
| Top Phase (g/L) | | | | | | | | |
| Ethanol | 70.9 | 139.3 | 221.2 | 268.7 | 278.5 | No phase separation for these ratios. | | |
| ⅔Methyl 1-Butanol | 636.0 | 559.4 | 498.2 | 410.2 | 267.1 | | | |
| Isobutanol | 0.0 | 0.0 | 1.6 | 1.3 | 1.3 | | | |
| n-butanol | 0.0 | 0.0 | 0.0 | 13.4 | 8.8 | | | |
| n-Pentanol | 0.0 | 0.0 | 0.0 | 0.0 | 0.0 | | | |
| Water | 126.9 | 134.6 | 104.1 | 136.0 | 305.6 | | | |
| Bottom Phase (g/L) | | | | | | | | |
| Ethanol | 101.7 | 128.4 | 181.1 | 210.4 | 218.6 | | | |
| ⅔Methyl 1-Butanol | 19.9 | 21.2 | 29.6 | 39.0 | 69.5 | | | |
| Isobutanol | 0.1 | 0.1 | 0.2 | 0.2 | 0.3 | | | |
| n-butanol | 1.8 | 1.7 | 1.9 | 2.3 | 3.0 | | | |
| n-Pentanol | 0.0 | 0.0 | 0.0 | 0.0 | 0.0 | | | |
| Water | 844.1 | 808.8 | 731.4 | 682.2 | 633.3 | | | |
| Volumes | | | | | | | | |
| Isoamyl Alcohol added (mL) | 50.0 | 20.0 | 10.0 | 12.0 | 20.0 | | | |
| Fusel Oil added (mL) | 10.0 | 10.0 | 10.0 | 18.0 | 40.0 | | | |
| Top Phase (mL) | 56.2 | 26.1 | 16.2 | 24.5 | 59.0 | | | |
| Bottom Phase (mL) | 3.8 | 3.9 | 3.5 | 5.5 | 1.0 | | | |
| Volume Percent of Iso OH | 83.3% | 66.7% | 50.0% | 40.0% | 33.3% | | | |
| Percent of Fusel IsoOH extracted | 86.5% | 85.2% | 81.5% | 78.7% | 96.9% | | | |
| Percent of Fusel EtOH extracted | 89.9% | 87.0% | 83.5% | 83.2% | 98.6% | | | |

TABLE 4

Summary of isoamyl acetate extraction experiments after phase separation.

| | Ratio of Fusel Oil to Isoamyl Acetate (solvent) | | | | | | | |
|---|---|---|---|---|---|---|---|---|
| | 1 to 5 | 1 to 2 | 1 to 1 | 1.5 to 1 | 2 to 1 | 3 to 1 | 4 to 1 | 5 to 1 |
| Top Phase (g/L) | | | | | | | | |
| Ethanol | No data | 118.0 | 202.5 | 228.7 | 284.3 | 308.2 | 316.3 | No phase separation |
| ⅔Methyl 1-Butanol | | 95.1 | 108.9 | 109.7 | 117.0 | 108.9 | 92.8 | |
| isobutanol | | 0.0 | 1.3 | 1.2 | 1.4 | 1.2 | 0.0 | |
| n-butanol | | 0.0 | 0.2 | 0.0 | 0.0 | 0.0 | 0.0 | |
| n-Pentanol | | 0.0 | 0.0 | 0.0 | 0.0 | 0.0 | 0.0 | |
| Isoamyl Acetate | | 563.3 | 450.0 | 424.0 | 337.4 | 243.6 | 165.5 | |
| n-butyl Acetate | | 51.7 | 43.4 | 14.7 | 31.0 | 21.9 | 14.7 | |
| Water | | 31.5 | 44.2 | 72.8 | 73.4 | 170.7 | 279.1 | |
| Bottom Phase (g/L) | | | | | | | | |
| Ethanol | | 76.8 | 196.1 | 185.5 | 214.5 | 240.8 | 264.6 | |
| ⅔Methyl 1-Butanol | | 2.4 | 7.8 | 8.3 | 10.0 | 19.1 | 32.6 | |
| isobutanol | | 0.1 | 0.1 | 0.2 | 0.2 | 0.3 | 0.5 | |
| n-butanol | | 0.5 | 1.2 | 1.0 | 1.3 | 0.4 | 1.9 | |
| n-Pentanol | | 0.0 | 0.0 | 0.0 | 0.0 | 0.0 | 0.0 | |
| Isoamyl Acetate | | 0.2 | 5.4 | 0.7 | 8.1 | 18.9 | 39.4 | |
| n-butyl Acetate | | 0.2 | 0.8 | 0.8 | 1.0 | 2.2 | 4.0 | |
| Water | | 898.5 | 733.2 | 751.5 | 703.5 | 646.3 | 572.0 | |
| Volumes | | | | | | | | |
| Isoamyl Acetate added (mL) | | 20.0 | 15.0 | 12.0 | 10.0 | 7.5 | 6.0 | |
| Fusel Oil added (mL) | | 10.0 | 15.0 | 18.0 | 20.0 | 22.5 | 24.0 | |
| Top Phase (mL) | | 24.0 | 22.0 | 21.0 | 20.9 | 24.2 | 27.5 | |
| Bottom Phase (mL) | | 6.0 | 8.0 | 9.0 | 9.1 | 5.8 | 2.5 | |
| Volume Percent of IsoAc | | 80.0% | 66.7% | 50.0% | 40.0% | 33.3% | | |
| Percent of Fusel extracted | | 97.4% | 92.6% | 92.6% | 91.9% | 91.2% | | |
| percent of EtOH in Fusel extracted | | 88.0% | 72.8% | 75.8% | 74.6% | 83.8% | | |

The results from the two extraction experiments are listed in Table 4 and shown in FIG. 1. In each case it can be seen that relatively high efficiency of extraction of the isoamyl alcohol from the initial fusel stream into the extractant phase is achieved. For all cases studied, over 80% of the isoamyl alcohol was recovered in the extractant phase. The main point of difference occurs is the extraction properties of ethanol. The isoamyl alcohol offers no separation of the ethanol from the isoamyl alcohol. This feature means that a large volume of ethanol will have to be treated in subsequent steps. The use of isoamyl acetate, on the other hand, offers extremely high recovery of the isoamyl alcohol (in excess of 91% in all cases studied) and lower levels of ethanol extracted in the upper phase. (as low as 72%).

Since isoamyl acetate does not appear in the fermentation, there is a need to develop a system to produce it. Two options are provided in FIGS. 2 and 3. In the first case a stream 1 from the ethanol distillation plant is sent to an extractor, which could be a continuous column or batch extractor. The incoming extraction liquid is in stream 5. The concentrated fusel oil stream leaving the extractor is in stream 2 and the spent fusel oil stream leaving the extractor in stream 6 is returned to the ethanol distillation column. Stream 2 is reacted with acetic acid in stream 4, in a reactive distillation column. The exiting streams 3 and 5 contain ethyl acetate/water and isoamyl acetate/some unreacted isoamyl alcohol, respectively. Stream 5 is then split to take off some of the isoamyl acetate as product and the remainder is recycled to be used as the extractant.

TABLE 5

| Stream | IsoOH | IsoAc | EtOH | EtAc | H2O | Acetic Acid | Other Ohs |
|---|---|---|---|---|---|---|---|
| | FIG. 1 (grams) | | | | | | |
| 1 | 112.130 | 0.000 | 767.510 | 0.000 | 883.995 | 0.000 | 4.156 |
| 2 | 128.395 | 404.891 | 341.212 | 0.000 | 120.000 | 0.000 | 26.400 |
| 3 | 0.000 | 157.521 | 34.121 | 587.285 | | 0.000 | 0.000 |
| 4 | 0.000 | 0.000 | 0.000 | 0.000 | 0.000 | 1064.398 | 0.000 |
| 5 | 16.265 | 404.891 | 0.000 | 0.000 | 120.000 | 585.419 | 0.000 |
| 5 out | 0.000 | 0.000 | 0.000 | 0.000 | 0.000 | 585.419 | 0.000 |
| 5 into extractor | 16.265 | 404.891 | 0.000 | 0.000 | | 0.000 | 0.000 |
| 6 | 12.034 | 9.661 | 257.448 | 0.000 | 763.995 | 0.000 | 30.556 |
| | In moles | | | | | | |
| 1 | 1.272 | 0.000 | 16.660 | 0.000 | 49.111 | 0.000 | |
| 2 | 1.456 | 3.110 | 7.406 | 0.000 | 6.667 | 0.000 | |
| 3 | 0.000 | 1.210 | 0.741 | 6.666 | 0.000 | 0.000 | |
| 4 | 0.000 | 0.000 | 0.000 | 0.000 | 0.000 | 17.725 | |
| 5 | 0.184 | 3.110 | 0.000 | 0.000 | 6.667 | 9.749 | |

TABLE 5-continued

| Stream | IsoOH | IsoAc | EtOH | EtAc | H2O | Acetic Acid | Other Ohs |
|---|---|---|---|---|---|---|---|
| 5 out | 0.000 | 0.000 | 0.000 | 0.000 | 0.000 | 9.749 | |
| 5 into extractor | 0.184 | 3.110 | 0.000 | 0.000 | 0.000 | 0.000 | |
| 6 | 0.136 | 0.074 | 5.588 | 0.000 | 42.444 | 0.000 | |

Figure 3:
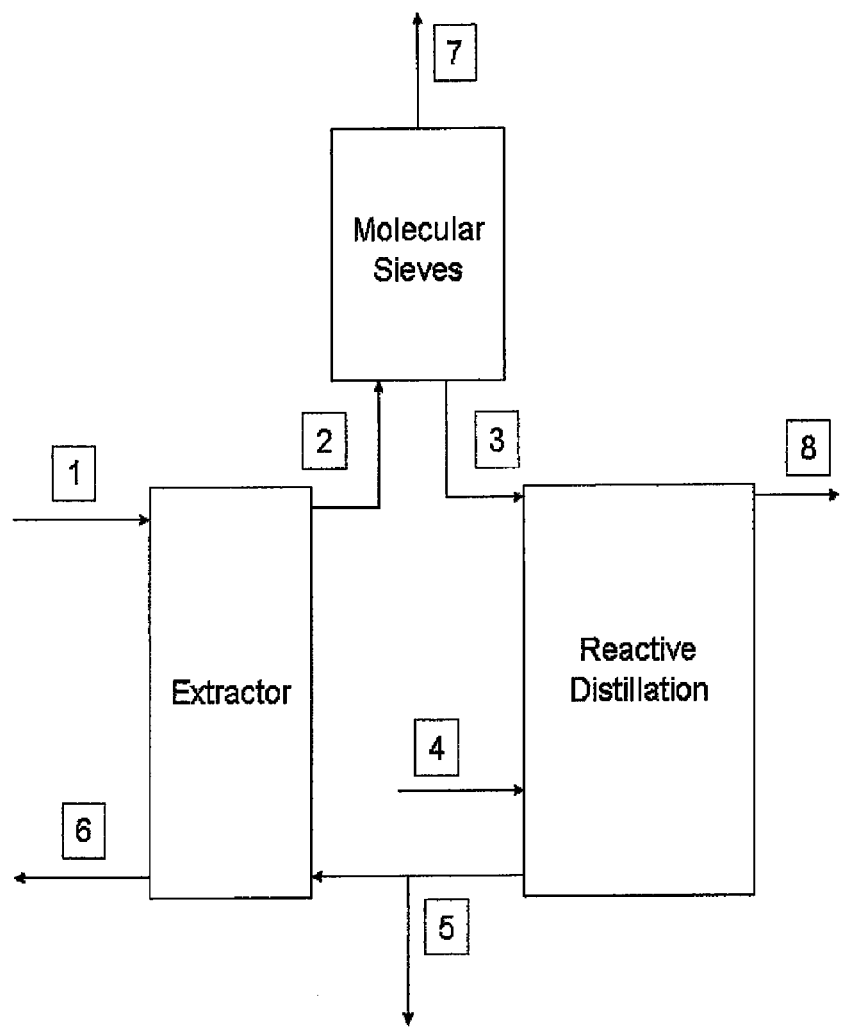
FIG. 3 is a schematic of a process where all of the ethanol is returned to a distillation plant and production of ethyl acetate is avoided.

In some cases it is preferred not to make ethyl acetate, but to retain ethanol. This may be due to a business decision or a regulatory restriction (e.g. Alcohol Fuel Plants cannot use the ethanol for production of chemicals). FIG. 3 addresses this case, where in the separation used to remove the ethanol is shown as a molecular sieve; however, other possible separations can be used here, e.g. distillation, pervaporation, etc. An approximate material balance is shown for the process in Table 6.

An improved process, based on extraction using higher alcohols and esters, as opposed to decantation, is proposed for the recovery of isoamyl alcohol and other fusel alcohols from an ethanol production plant. This process does not introduce water in the decantation step resulting in a significant reduction of energy use.

In the certain embodiments, isoamyl acetate is used as the extractant ester because it provides for high recovery of fusel alcohols and leaves more ethanol in the aqueous phase that is recycled back into the ethanol production process.

TABLE 6

Figure 2:
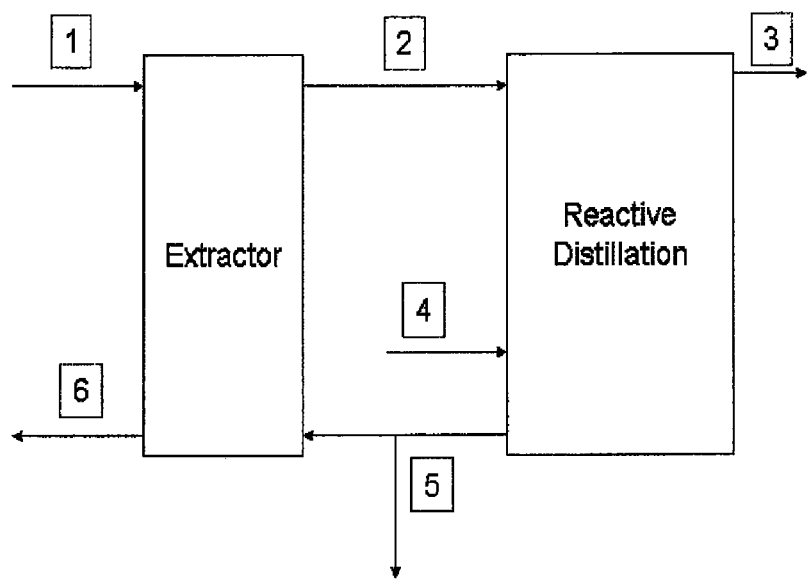
FIG. 2 is a schematic of a process where ethyl acetate can be marketed as a chemical.

| Stream | IsoOH | IsoAc | EtOH | EtAc | H2O | Acetic Acid | Other Ohs |
|---|---|---|---|---|---|---|---|
| FIG. 2 (grams) | | | | | | | |
| 1 | 112.130 | 0.000 | 767.510 | 0.000 | 883.995 | 0.000 | 4.156 |
| 2 | 128.395 | 404.891 | 341.212 | 0.000 | 120.000 | 0.000 | 26.400 |
| 3 | 128.395 | 404.891 | 0.000 | 0.000 | 100.000 | 0.000 | 0.000 |
| 4 | 0.000 | 0.000 | 0.000 | 0.000 | 0.000 | 174.892 | 0.000 |
| 5 | 16.265 | 562.412 | 0.000 | 0.000 | 120.000 | 96.191 | 0.000 |
| 5 out | 0.000 | 157.521 | 0.000 | 0.000 | 0.000 | 96.191 | 0.000 |
| 5 intoextractor | 16.265 | 404.891 | 0.000 | 0.000 | 0.000 | 0.000 | 0.000 |
| 6 | 12.034 | 9.661 | 257.448 | 0.000 | 763.995 | 0.000 | 30.556 |
| 7 | 0.000 | 0.000 | 341.212 | 0.000 | 20.000 | 0.000 | 0.000 |
| In moles | | | | | | | |
| 1 | 1.272 | 0.000 | 16.660 | 0.000 | 49.111 | 0.000 | |
| 2 | 1.456 | 3.110 | 7.406 | 0.000 | 6.667 | 0.000 | |
| 3 | 1.456 | 3.110 | 0.000 | 0.000 | 5.556 | 0.000 | |
| 4 | 0.000 | 0.000 | 0.000 | 0.000 | 0.000 | 2.912 | |
| 5 | 0.184 | 4.320 | 0.000 | 0.000 | 6.667 | 1.602 | |
| 5 out | 0.000 | 1.210 | 0.000 | 0.000 | 0.000 | 1.602 | |
| 5 intoextractor | 0.184 | 3.110 | 0.000 | 0.000 | 0.000 | 0.000 | |
| 6 | 0.136 | 0.074 | 5.588 | 0.000 | 42.444 | 0.000 | |
| 7 | 0 | 0 | 7.406 | 0 | 1.111 | 0 | |

Isoamyl alcohol is a preferred alcohol extractant for recovery of fusel alcohols.

The isoamyl acetate extractant can be produced and recycled using reactive distillation.

The process can be used with streams from Distilled Spirits Plants and Alcohol Fuel Plants.

Many modifications and variations of the present disclosure are possible in light of the above teachings. Therefore, within the scope of the appended claims, the present disclosure may be practiced other than as specifically described.

What is claimed is:

1. A process for recovering amyl alcohol from a product stream of an ethanol distillation apparatus, comprising:
   (a) conveying a first fluid stream from an ethanol distillation apparatus to an extractor, the first fluid stream consisting of a first fluid phase comprising amyl alcohol in admixture with an ethanol in water solution;
   (b) conveying a second fluid stream to the extractor, the second fluid stream being immiscible with the first fluid stream and consisting of a second fluid phase comprising at least one extractant solvent selected from the group consisting of an amyl alcohol and an amyl alcohol acetate;
   (c) contacting the first fluid phase with the second fluid phase in the extractor, thereby extracting the amyl alcohol from the first fluid phase into the second fluid phase;
   (d) separating the immiscible fluid phases; and
   (e) separating the extractant solvent from the second fluid phase.

2. The process of claim 1 wherein the extractant solvent is amyl acetate.

3. The process of claim 1 wherein the extracted amyl alcohol comprises a mixture of 2-methyl-butanol and 3-methyl-butanol.

4. The process of claim 1 wherein the first phase comprises fusel oil from an ethanol fermentation process.

5. The process of claim 4 wherein at least 80% of the fusel oil is extracted from the first phase.

6. The process of claim 1 wherein isoamyl acetate is extracted from the first fluid phase.

7. The process of claim 1 wherein the extractant solvent is isoamyl acetate.

8. A process for extracting fusel alcohols from a product stream of an ethanol production plant, comprising contacting the product stream with a fluid phase containing an extractant, whereby fusel alcohols are extracted from the product stream into the fluid phase containing the extractant, and wherein water is not introduced in a decantation step.

9. The process of claim 8 wherein isoamyl acetate is the extractant.

10. The process of claim 8 wherein isoamyl alcohol is the extractant.

11. The process of claim 9 wherein the isoamyl acetate extractant is produced using reactive distillation.

12. The process of claim 8 wherein the product stream is from a Distilled Spirits Plant and/or an Alcohol Fuel Plant.

13. A process for extracting fusel alcohols from a product stream of an ethanol distillation apparatus, the product stream comprising an admixture of water, ethanol and fusel alcohols, compising:
   adding to the admixture an extractant solvent selected from amyl alcohols, amyl acetates, and mixtures of amyl alcohols and amyl acetates, thereby producing a two-phase system including a first phase comprised predominately of water and ethanol, and a second phase immiscible with the first phase and comprised predominately of amyl alcohols, amyl acetates, or a mixture of amyl alcohols and amyl acetates;
   allowing contact between the first phase and the second phase to cause transfer of fusel alcohols in the first phase to the second phase; and
   separating the first and second phases from each other.

14. A process in accordance with claim 13, wherein the extractant solvent comprises an amyl alcohol.

15. A process in accordance with claim 13, wherein the fusel alcohols comprise amyl alcohols.

16. A process in accordance with claim 15, where the amyl alcohols comprise 2-methyl-butanol and 3-methyl-butanol.

17. A process in accordance with claim 13, wherein at least 80% of the fusel alcohols in the admixture prior to addition of the extractant solvent are transferred to the second phase prior to separating the first and second phases from each other.

18. A process in accordance with claim 13, wherein the extractant solvent comprises an isoamyl acetate.

19. A process in accordance with claim 13, wherein, after the first and second phases are separated from each other, the extractant solvent is used in a reactive distillation process to produce isoamyl acetate that can be used for subsequent extraction.

20. A process in accordance with claim 19, wherein acetic acid is added during the reactive distillation to produce isoamyl acetate.

\* \* \* \* \*